United States Patent [19]

Hochberg

[11] Patent Number: 5,054,924
[45] Date of Patent: Oct. 8, 1991

[54] METHOD FOR EXTRACTING LONG-EQUIVALENT WAVELENGTH INTERFEROMETRIC INFORMATION

[75] Inventor: Eric B. Hochberg, Altadena, Calif.

[73] Assignee: California Institute of Technology, Pasadena, Calif.

[21] Appl. No.: 484,247

[22] Filed: Feb. 26, 1990

Related U.S. Application Data

[63] Continuation-in-part of Ser. No. 364,165, Jun. 12, 1989.

[51] Int. Cl.$^5$ ............................................. G01B 4/02
[52] U.S. Cl. .................................. 356/359; 356/360
[58] Field of Search .............................. 356/359, 360

[56] References Cited

U.S. PATENT DOCUMENTS 4,832,489  5/1989  Wyant et al. ...................... 356/359

Primary Examiner—Davis L. Willis
Assistant Examiner—Matthew W. Koren
Attorney, Agent, or Firm—Leonard Tachner

[57] ABSTRACT

A process for extracting long-equivalent wavelength interferometric information from a two-wavelength polychromatic or achromatic interferometer. The process comprises the steps of simultaneously recording a non-linear sum of two different frequency visible light interferograms on a high resolution film and then placing the developed film in an optical train for Fourier transformation, low pass spatial filtering and inverse transformation of the film image to produce low spatial frequency fringes corresponding to a long-equivalent wavelength interferogram. The recorded non-linear sum irradiance derived from the two-wavelength interferometer is obtained by controlling the exposure so that the average interferogram irradiance is set at either the noise level threshold or the saturation level threshold of the film.

10 Claims, 3 Drawing Sheets

5,054,924

METHOD FOR EXTRACTING LONG-EQUIVALENT WAVELENGTH INTERFEROMETRIC INFORMATION

ORIGIN OF INVENTION

The invention described herein was made in the performance of work under a NASA contract, and is subject to the provisions of Public Law 96-517 (35 USC 202) in which the Contractor has elected to retain title.

CROSS REFERENCE TO RELATED APPLICATIONS

This application is an continuation-in-part of patent application Ser. No. 07/364,165 filed June 12, 1989.

TECHNICAL FIELD

The present invention relates generally to interferometric optical systems and more specifically to a method for extracting long-equivalent wavelength interferometric information. Such information is initially derived using a two-wavelength interferometer such as disclosed in application Ser. No. 07/364,165 of which the present application is a continuation-in-part.

BACKGROUND ART

The wavelength independent interferometer disclosed in the parent of which the present application is a continuation in part discloses a polychromatic interferometer in which, in one embodiment, the output beams of two lasers are coaxially combined in the polychromatic interferometer to produce two independent and superimposed-in-registration interferograms of the one optical component under test. This interferometer admits the possibility of forming a long equivalent wavelength interferogram corresponding to a synthetic wavelength which is equal to the product of the two operational wavelengths divided by the difference. Since the spatial frequency of the fringe pattern associated with any particular source wavelength is inversely related to that wavelength, a simpler relationship between component and derived interferograms exists: The spatial frequency of the long equivalent wavelength interferogram is simply the difference in spatial frequencies associated with the two component wavelengths. Consequently, the apparent or effective frequency of the combined laser light is significantly lower than the actual frequency of the visible light of each such laser. The present invention relates to a process for extracting the information of such a two-wavelength interferogram to produce a long-equivalent wavelength interferogram. The interference or fringe pattern of the resulting interferogram would have been derived directly had a laser or other light source of a frequency equal to the difference between the two actually used laser frequencies been utilized instead. The above-derived long-equivalent wavelength interferogram is then suitable for conventional fringe processing whereby the surface topography or wavefront distortion associated with the component under test—for example, an aspheric surface such as the human cornea may be extracted.

The most straightforward method for extracting long equivalent wavelength information is by means of a multiplicative combination of the two fundamental interferograms. When, for example, two interferograms are combined multiplicatively, the product interferogram may be decomposed into four component interferograms: Two interferograms have fringe spatial frequencies corresponding to the inverse of each of the two component wavelengths and two additional interferograms having fringe spatial frequencies corresponding to sum and difference fringe spatial frequencies. This last difference spatial frequency corresponds to the long equivalent wavelength interferogram of interest.

As such, this product interferogram is amenable to spatial filtering techniques in the Fourier plane whereby, with the appropriate Fourier transform optics, spatial filtering and inverse transformation optics, a interferogram containing only the long equivalent wavelength information is produced. This in turn admits the use of a lower spatial resolution detector commensurate with the sensitivity reduction associated with the "coarser" long equivalent wavelength fringes.

There are at least two ways one may realize the product interferogram. One such way is by serial recording: Specifically, the first interferogram is recorded, developed and then "played back" with interferogram number two. This however, is not a particularly useful technique if the object being subjected to the interferogram measurement technique is not stationary as in the case for example of keratometers used for in-vivo measurements of the human cornea wherein the results will reflect a combination of surface topography as well as motion effects. An additional, possible multiplicative technique comprises parallel recording wherein the two different wavelength interferograms are formed on separate high spatial resolution detectors and then multiplied in the digital domain.

One possible alternative to multiplicative techniques is some form of extraction method that relies on the summing of the two interferograms. In fact, the invention disclosed in the aforementioned parent application is particularly appropriate for use in summing techniques for information extraction. The interferometer described therein is capable of producing a single interferogram which is the sum of the two interferograms that would otherwise be derived at the independent wavelengths of the two laser sources. Unfortunately, simply adding the two interferograms together does not produce the desired information. More specifically, when two interferograms are present simultaneously and are spatially superimposed, a single detector can record only the incoherent sum of the irradiances and thus the sum contains no more information than a DC component and components with spatial frequencies corresponding to the individual wavelengths operating in the interferogram. A simple sum does not produce any frequency components corresponding to the sum or difference of the frequencies of the independent sources and the lack of any different frequency components in that sum means that there is no long-equivalent wavelength interferometric information that can be extracted therefrom.

There is therefore a need for an extraction process for use with a long equivalent wavelength interferometer which avoids the aforementioned deficiencies of multiplicative processes and which exploits the summing characteristic of spatially superimposed interferograms such as may be readily provided by the wavelength independent interferometer disclosed in the aforementioned parent application.

SUMMARY OF THE INVENTION

The present invention overcomes the aforementioned deficiencies of the multiplicative process by exploiting the information on a single interferogram produced simultaneously at two different wavelengths such as in the manner described in the disclosure of the parent application hereof. More specifically, the present invention comprises an information extraction process in which a non-linear recording of the sum interferogram as provided by a polychromatic interferometer on high resolution film, may be utilized to extract long-equivalent wavelength interferometric information. When the sum interferogram exposure is adjusted to fall in a non-linear portion of the high resolution recording film, a Fourier transform of the resulting record reveals both sum and difference spatial frequencies. The latter corresponds precisely to the long-equivalent wavelength interferometric information. Once this film is processed, it may be put into a conventional spatial filtering optical train which provides Fourier transformation, low pass spatial filtering and inverse transformation, the output of which comprises a filtered version of the original two-wavelength interferogram, but with only the difference frequency component present. This difference frequency component corresponds to the long-equivalent wavelength interferometric information desired. Thus, as a result of the unique process of the present invention, a non-linear recording of the sum interferogram can be processed in the same manner as a multiplicative interferogram to reveal the long-equivalent wavelength information of interest.

OBJECTS OF THE INVENTION

It is therefore a principal object of the present invention to provide a process for extracting long-equivalent wavelength interferometric information from a single sum interferogram derived from a two-wavelength interferometer.

It is an additional object of the present invention to provide a process for extracting long-equivalent wavelength interferometric information without requiring any form of multiplicative process that would require the use of two independent single frequency interferograms.

It is still an additional object of the present invention to provide an improved method for extracting long-equivalent wavelength interferometric information that is especially adapted for use with a polychromatic interferometer for measuring the topography of the human cornea.

It is still an additional object of the present invention to provide an improved method for use in topographically mapping a reflective surface wherein a dual-wavelength sum fringe pattern is provided by a wavelength-independent interferometer.

It is still an additional object of the present invention to provide a method for extracting a non-ambiguous difference frequency fringe pattern from a wavelength-independent optical interferometer without using multiplicative processing.

BRIEF DESCRIPTION OF THE DRAWINGS

The aforementioned objects and advantages of the present invention, as well as additional objects and advantages thereof, will be more fully understood as a result of a detailed description of a preferred embodiment when taken in conjunction with the following drawings in which.

DETAILED DESCRIPTION OF A PREFERRED EMBODIMENT

Figure 1:
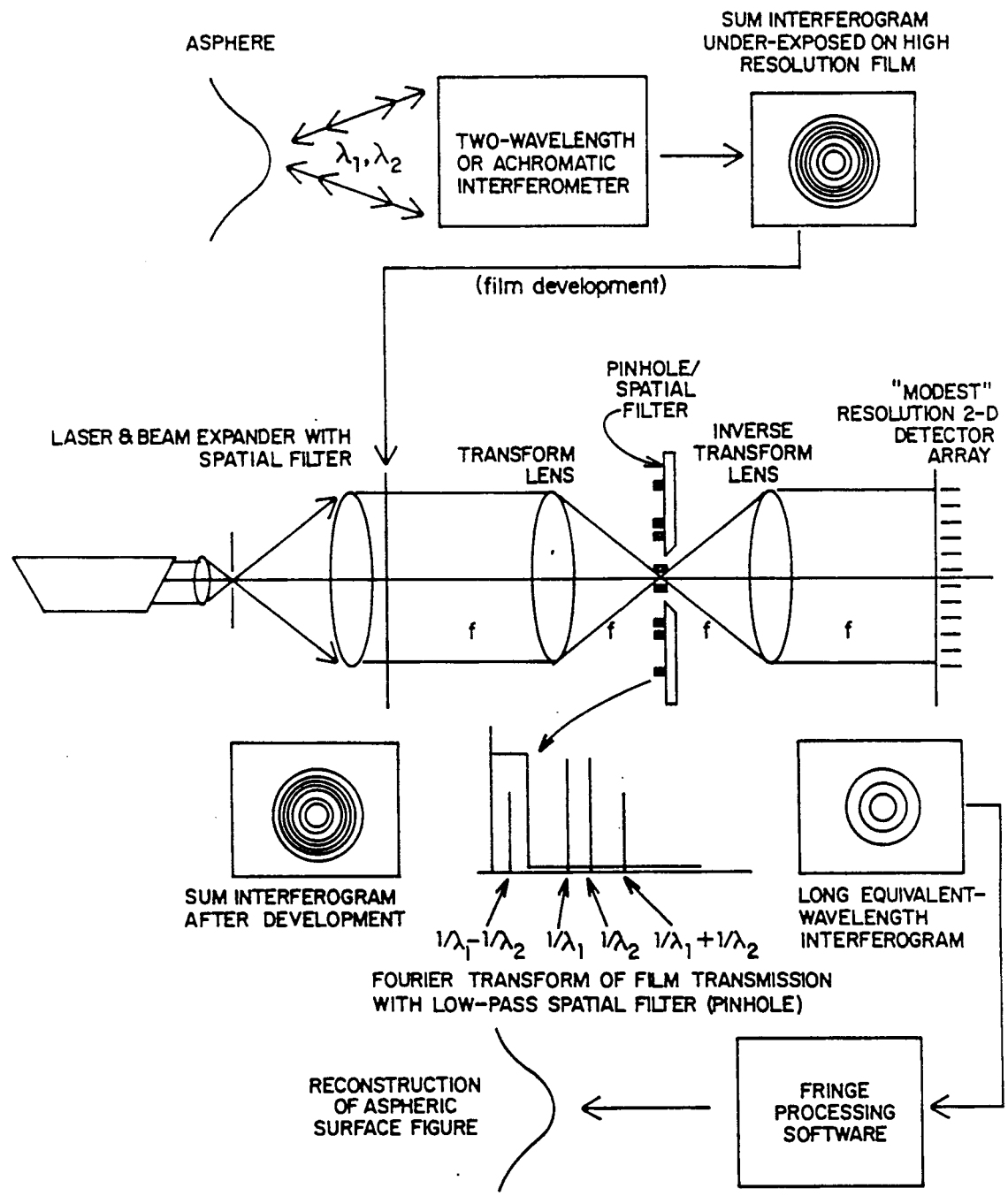
FIG. 1 is a block diagram of an aspheric testing scheme which includes the process of the present invention.

Referring now to FIG. 1, it will be seen that the process of the present invention is designed to be used in conjunction with a polychromatic or achromatic interferometer such as for measuring the topography of an aspherical surface such as the cornea of the human eye. One polychromatic or achromatic interferometer is disclosed in detail in patent application Ser. No. 07/364,165 filed on June 12, 1989 of which the present invention is a continuation in part. The disclosure of the aforementioned parent application is incorporated herein by reference and should be considered a part of the disclosure of the present invention. However, it will be understood that the present invention is not limited for operation with the wavelength-independent interferometer disclosed in the parent application. The present invention comprises a process which can be used with other polychromatic or achromatic interferometers, or for that matter any interferometer capable of producing a sum interferogram generated using two different wavelength light sources from which it is desired to extract a long-equivalent wavelength interferogram.

Figure 2:
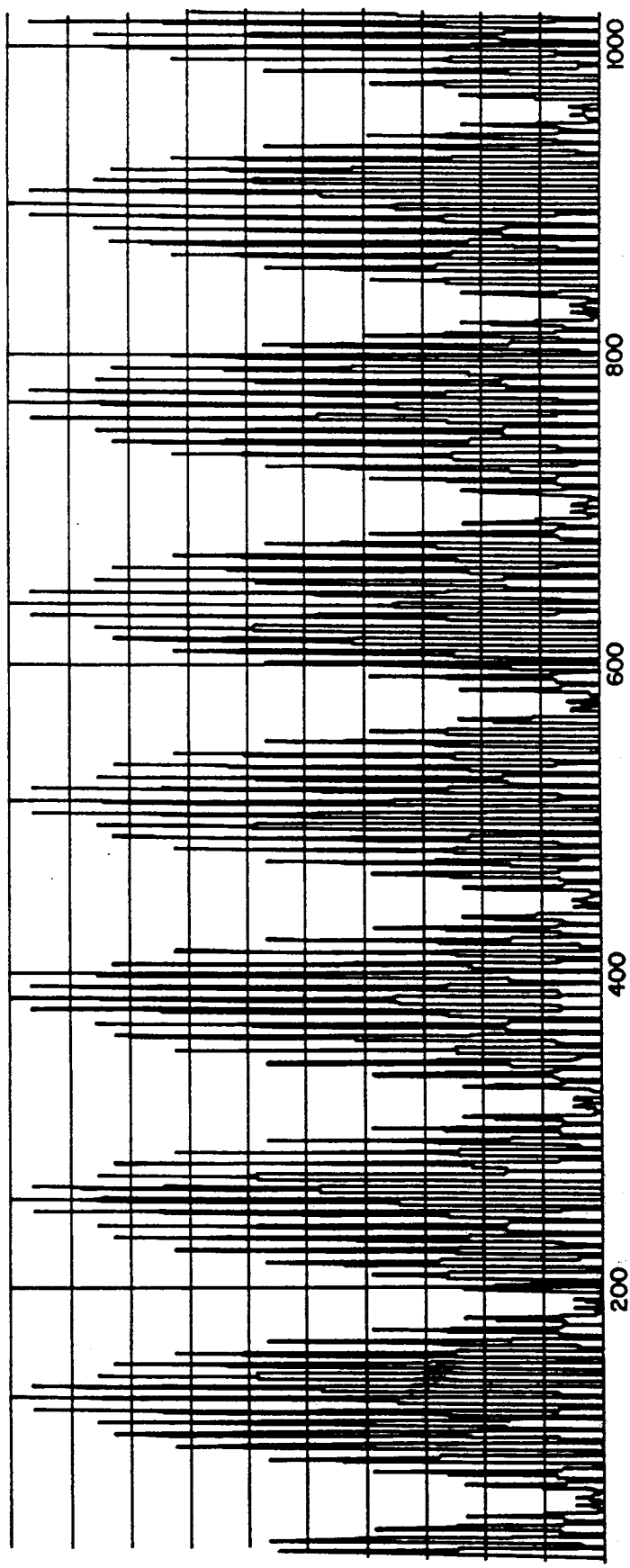
FIG. 2 is a graphical representation of the non-linear sum of interferometer fringe patterns used to explain a step in the process of the present invention.
Figure 3:
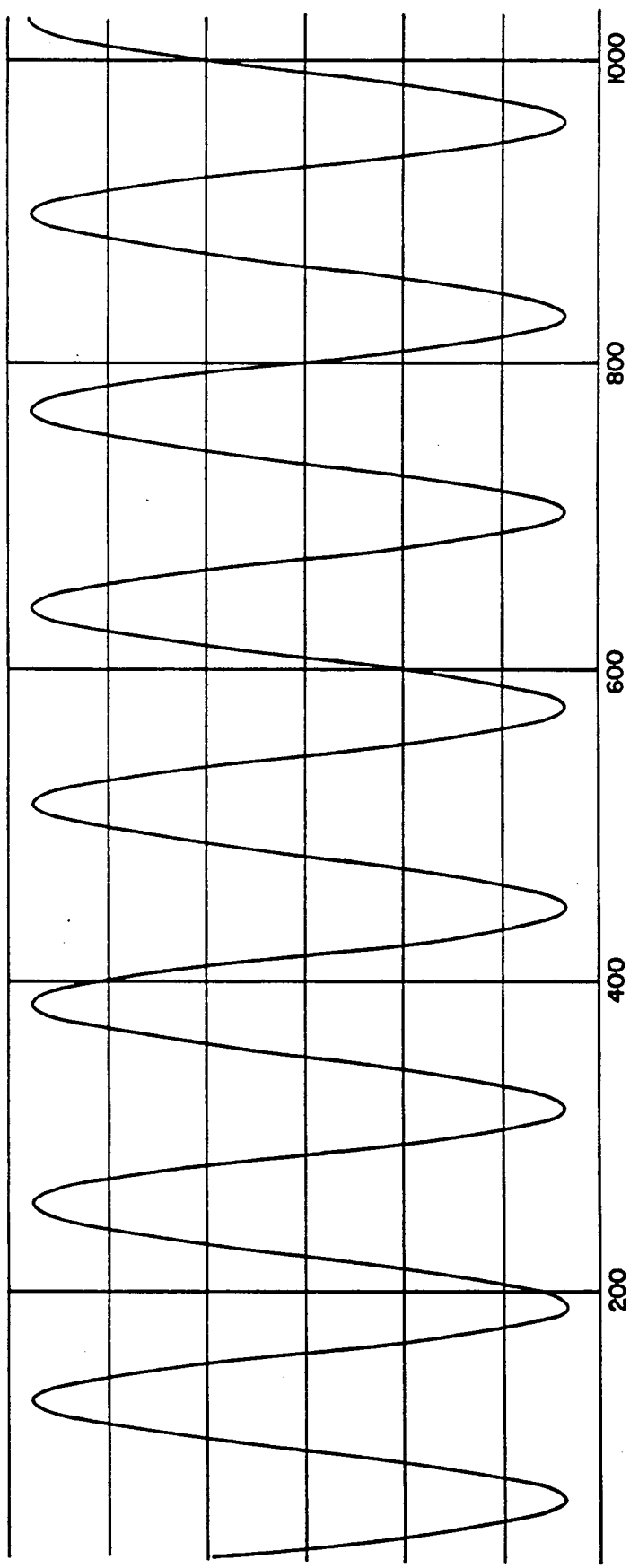
FIG. 3 is a graphical representation of a spatially-filtered, non-linearly processed sum interferogram which corresponds to a result produced by the process of the present invention.

The first step of the process of the present invention comprises the step of producing a simultaneous non-linear recording of the sum of two visible light interferograms on high resolution film. Although any high resolution film may be appropriate for use with the present invention, in a preferred embodiment of the invention, such film is preferably high resolution instant film such as Xerox Dry Micro-Film sold under the trademark XDM. This film is a high resolution selenium and thermoplastic-based material and has an extremely fine grain characteristic that constitutes a high resolution photoreceptor especially suitable for use in the invention. The term non-linear recording as used in the present invention, refers to a non-linear recording of the sum irradiance in which the average interferogram irradiance is set at either the noise ("fog") or saturation exposure level of the photo receptor or film. FIG. 2 shows the non-linear sum of interferometric patterns where the average irradiance has been set at the noise level of the film, meaning the interferogram has been underexposed on the film. The results obtained in the present invention by setting the average irradiance at the saturation level should be qualitatively identical. However, from a radiometric and clinical standpoint, the underexposure technique would be the most desirable way to introduce the necessary non-linearity to produce a clipped sum interferogram, the equivalent waveform of which is shown in FIG. 2 for a tilted plano surface.

Those having skill in the art to which the present invention pertains will understand that the Fourier transform of the clipped sum interferogram waveform of FIG. 2, contains both sum and difference frequencies. The difference frequency in the spatial domain is the envelope of the waveform shown in FIG. 2. It is this envelope in the spatial domain which the remaining steps of this process are designed to produce.

These remaining steps consist of Fourier transformation, spatial filtering and inverse transformation of the high resolution non-linear sum interferogram film record produced by the aforementioned first step of the process. These steps may be carried out in the manner shown in FIG. 1 by placing the sum interferogram in a Fourier transformation, spatial filtering and inverse transformation optical train.

As shown in FIG. 1, this optical train consists of a source of coherent monochromatic collimated illumination, a Fourier transform lens, an inverse transform lens and a pinhole or spatial filter which is placed at the Fourier plane between the transform lens and the inverse transform lens. The spatial filter is designed to pass only the difference frequency component and to block the sum frequency component, as well as the individual frequency components of the waveform of FIG. 2. As a consequence thereof, the output of the inverse transform lens of FIG. 1 is a low pass, filtered interferogram which may be readily detected by means of a low resolution CCD array to reveal the long-equivalent wavelength interferogram of interest. Standard static fringe interpretation software may then be applied to the output of the low resolution detector array to yield the output of interest, namely, the wavefront distortion or surface topology of a cornea or other aspheric surface being measured by the interferometer of FIG. 1.

Thus, it will be seen that the processing technique described above, allows the use of practical detector arrays for the testing of strongly aspheric surfaces. Although, high resolution film should be used to record the original sum interferogram, the detector need only have sufficient resolution for the highest long-equivalent wave interferogram fringe frequency expected from the surface. The Fourier transformation filtering and inverse transforming optical train shown in FIG. 1, may for example be a model FX15/5F Fourier transform system available from Space Optics Research Labs of Chelmsford Massachusetts, when combined with a suitable spatial filter or pinhole, the diameter of which is selected to pass only the difference frequencies at the Fourier plane as described above.

It will now be understood that what has been disclosed herein comprises a process for extracting long-equivalent wavelength interferometric information from a polychromatic or achromatic interferometer. The process comprises the steps of simultaneously recording in a non-linear fashion the sum of two different wavelength interferograms on a high resolution film and then placing the developed film in an optical train for Fourier transformation, low pass spatial filtering and inverse transformation of the film image to produce low spatial frequency fringes corresponding to a long-equivalent wavelength interferogram. The recorded non-linear sum irradiance derived from the two-wavelength interferometer is obtained by controlling the exposure so that the average interferogram irradiance is set at either the noise level exposure threshold or the saturation level exposure threshold of the film.

Those having skill in the art to which the present invention pertains, will now as a result of the applicant's teaching herein, perceive various modifications and additions which may be made to the invention. By way of example, the precise method for producing a non-linear sum interferogram recording, as well as the precise manner for spatially filtering the frequency domain transformation of the resulted image of such a recording, may be carried out in ways which differ from the disclosed preferred embodiment of the invention. Accordingly, all such modifications and additions are deemed to be within the scope of the invention which is to be limited only by the claims appended hereto.

I claim:

1. A method for extracting long-equivalent wavelength interferometric information from a wavelength-independent sum interferometer; the method comprising the steps of:
   a) preparing a non-linear sum two-wavelength interferogram;
   b) placing the interferogram prepared in step a) in a Fourier transform, spatial filter, inverse Fourier transform optical train; and
   c) detecting the output image of said optical train.

2. The method recited in claim 1 wherein step a) comprises the steps of the exposing the two-wavelength sum fringe pattern of said interferometer on a high resolution film with the exposure adjusted to fall in a non-linear portion of said film; and developing said film to produce a non-linear sum two-wavelength interferogram.

3. The method recited in claim 1 wherein step c) comprises the step of placing a CCD detector array in the optical path output of said optical train.

4. A method for use in topographically mapping a reflective surface; the method comprising the following steps:
   a) generating an interferometric fringe pattern from said surface with at least two distinct wavelengths of light reflected simultaneously from said surface;
   b) preparing a non-linear sum interferogram from said fringe pattern;
   c) obtaining an optical Fourier transform of said interferogram;
   d) spatially filtering out all frequency components of said Fourier transform except the components corresponding to the difference frequency between said two distinct wavelengths of light;
   e) obtaining an optical inverse Fourier transform of said spatially filtered Fourier transform; and
   f) detecting the optical inverse Fourier transform obtained in step e).

5. The method recited in claim 4 wherein step b) comprises the step of exposing said interferometric fringe pattern onto a high resolution film with the exposure thereof being such that the average irradiance of said pattern substantially coincides with the noise exposure level of said film.

6. The method recited in claim 4 wherein step b) comprises the step of exposing said interferometric fringe pattern onto a high resolution film with exposure thereof being such that the average irradiance of said pattern substantially coincides with the saturation exposure level of said film.

7. A method for extracting a non-ambiguous difference frequency fringe pattern from a two-wavelength optical interferometer; the method comprising the steps of:
   a) generating a non-linear sum interferogram from said interferometer;

b) placing the interferogram generated in step a) in a Fourier transform, spatial filter, inverse transform optical train wherein said spatial filter comprises a pinhole having an aperture dimension for passing only said difference frequency component.

8. The method recited in claim 7 wherein step a) comprises the steps of exposing the optical output of said interferometer on a film at an exposure level adjusted to a non-linear exposure portion of said film; and developing said film.

9. The method recited in claim 8 wherein the average of said adjusted exposure level corresponds to the noise threshold of said film.

10. The method recited in claim 8 wherein the average of said adjusted exposure level corresponds to the saturation threshold of said film.

* * * * *